US005558871A

United States Patent [19]
Griat et al.

[11] Patent Number: 5,558,871
[45] Date of Patent: Sep. 24, 1996

[54] COSMETIC AND/OR DERMATOLOGICAL COMPOSITIONS CONTAINING SALICYLIC ACID

[75] Inventors: Jacqueline Griat, Ablon; Elisabeth Picard, Velizy Villacoublay; Jean-Pierre Laugier, Antony, all of France

[73] Assignee: L'Oreal, Paris, France

[21] Appl. No.: 365,806

[22] Filed: Dec. 29, 1994

[30] Foreign Application Priority Data

Jan. 10, 1994 [FR] France .................. 94 00175

[51] Int. Cl.$^6$ .................. A61K 7/48; A61K 9/10
[52] U.S. Cl. .................. 424/401; 424/70.1; 424/405; 514/846; 514/847; 514/859; 514/937; 514/941; 514/944
[58] Field of Search .................. 424/401, 78.03, 424/405, 70.1; 514/846, 847, 859, 941, 937, 944, 159

[56] References Cited

U.S. PATENT DOCUMENTS

| | | | |
|---|---|---|---|
| 5,262,407 | 11/1993 | Leveque | 514/159 |
| 5,362,494 | 11/1994 | Zysman | 424/401 |

FOREIGN PATENT DOCUMENTS

| | | |
|---|---|---|
| 378936 | 7/1990 | European Pat. Off. . |
| 570230 | 11/1993 | European Pat. Off. . |
| 2174906 | 11/1986 | United Kingdom . |

*Primary Examiner*—Thurman K. Page
*Assistant Examiner*—Sharon Howard
*Attorney, Agent, or Firm*—Oblon, Spivak, McClelland, Maier, & Neustadt, P.C.

[57] ABSTRACT

The solubilization of salicylic acid derivatives, and in particular of 5-n-octanoylsalicylic acid, is achieved by mixing the salicylic acid derivative with a vegetable oil. The obtained compositions are useful, in particular, for treating acne and ageing.

18 Claims, No Drawings

COSMETIC AND/OR DERMATOLOGICAL COMPOSITIONS CONTAINING SALICYLIC ACID

BACKGROUND OF THE INVENTION

1. Field of the Invention

The present invention relates to a process for the solubilization of salicylic acid derivatives in at least one vegetable oil, and to cosmetic and/or dermatological compositions containing such a solubilized salicylic acid derivative. Such compositions can be used for treating the body and face, including the scalp and nails, and more especially for treating acne and skin ageing (wrinkles, fine lines, complexion). The present compositions can take the form of emulsions, oily solutions or dispersions of lipid vesicles.

2. Discussion of the Background

It is known to use salicylic acid derivatives as keratolytic agents for treating acne and as anti-ageing agents in cosmetic and/or dermatological compositions. Thus, FR 2,581,542 and EP 378,936 describe such derivatives.

These derivatives are of great importance on account of their biological effects on the skin. However, their use creates a problem, since they occur in crystalline form and are soluble neither in water nor in the oils traditionally used in the cosmetics field, such as mineral oils (petrolatum, paraffin). Thus, if such salicylic acid derivatives are introduced "as is" into cosmetic and/or dermatological compositions, they remain in the crystalline state, making the use of the composition containing them ineffective for treating the skin.

These derivatives are, on the other hand, soluble in lower alcohols such as ethanol or isopropanol, or in solvents such as octyldodecanol, some glycols, short-chain ($<C_{12}$) fatty alcohols or short-chain ($<C_{12}$) esters. Lower alcohols have the drawback of drying and irritating the skin, and it is hence preferable to avoid using them in body and/or face care products. Short-chain fatty alcohols and fatty esters and some glycols which enable these salicylic acid derivatives to be solubilized result in the penetration of active agents into the skin, which is not necessarily desirable in skin care products. Moreover, at the present time, there is, generally speaking, an increasing endeavor to limit the use of solvents in skin care products, since these solvents are not always well tolerated and can bring about irritation when used in excessively large amounts.

Thus, there remains a need for a method of solubilizing salicylic acid derivatives which overcomes these drawbacks. There also remains a need for cosmetic and/or dermatological compositions which contain solubilized salicylic acid derivatives.

SUMMARY OF THE INVENTION

Accordingly, it is one object of the present invention to provide a novel method for solubilizing salicylic acid derivatives.

It is another object of the present invention to provide novel cosmetic and/or dermatological compositions which contain a solubilized salicylic acid derivative.

It is another object of the present invention to provide a method for treating ageing of the skin by applying such a composition to the skin.

It is another object of the present invention to provide a method for treating acne by applying such a composition to the skin.

These and other objects, which will become apparent during the following detailed description, have been achieved by the inventors' discovery that vegetable oils solubilize salicylic acid derivatives and enable salicylic acid derivatives to be introduced into cosmetic and/or dermatological compositions without recrystallization of these derivatives taking place and without it being necessary to use a large amount of solvent. EP-A-570230 describes compositions containing a salicylic acid derivative and a vegetable oil, but the vegetable oil is used among another oily constituents and clearly in an insufficient quantity to solubilize the salicylic acid derivative.

The inventors have found, surprisingly, that only vegetable oils enable the salicylic acid derivatives to be solubilized; other oils, and especially mineral oils, do not enable this outcome, and the solubilization can be obtained only when the vegetable oil is present in an amount at least five times the quantity of salicylic acid derivative, based on weight.

DETAILED DESCRIPTION OF THE PREFERRED EMBODIMENTS

Thus, in a first embodiment, the present invention provides a process for the solubilization of a salicylic acid derivative, characterized in that it comprises mixing a vegetable oil with a salicylic acid derivative in a weight ratio of vegetable oil to salicylic acid derivative greater than 5. The weight ratio of vegetable oil to salicylic acid derivative is preferably greater than 10 and smaller than 99.

In particular, the salicylic acid derivative is preferred to have the formula (I):

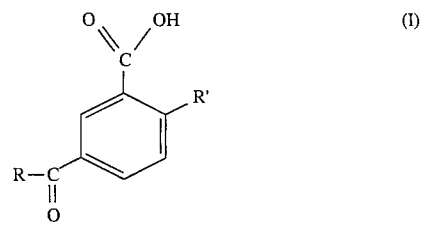

wherein:

R is a saturated linear, branched, or cyclic aliphatic group having from 3 to 11 carbon atoms; a linear branched, or cyclic unsaturated hydrocarbon group having from 3 to 17 carbon atoms and having one or more conjugated or unconjugated ethylenic double bonds; a saturated linear, branched, or cyclic aliphatic group having from 3 to 11 carbon atoms and substituted with at least one substituent selected from the group consisting of halogens, trifluoromethyl, hydroxyl, hydroxyl esterified with a carboxylic acid having from 1 to 6 carbon atoms, carboxyl, and carboxyl esterified with a lower alcohol having from 1 to 6 carbon atoms; or a linear, branched, or cyclic unsaturated hydrocarbon group having from 3 to 17 carbon atoms and having one or more conjugated or unconjugated ethylenic double bonds and substituted with at least one substituent selected from the group consisting of halogens, trifluoromethyl, hydroxyl, hydroxyl esterified with a carboxylic acid having from 1 to 6 carbon atoms, carboxyl, and carboxyl esterified with a lower alcohol having from 1 to 6 carbon atoms; and R' is a hydroxyl group or an ester function of formula (II):

wherein $R_1$ is a saturated or unsaturated aliphatic group having from 1 to 18 carbon atoms.

As preferred compounds of formula (I), 5-n-octanoylsalicylic acid and 5-n-dodecanoylsalicylic acid may be mentioned.

In another embodiment, the present invention also provides cosmetic and/or dermatological compositions containing a salicylic acid derivative, preferably of formula (I), solubilized in at least one vegetable oil.

As vegetable oils which can be used in the present invention, there may be mentioned the oils obtained from flowers, fruits or plant leaves, and in particular sunflower oil, sunflower hybrid oil, wheat-germ oil, jojoba oil, maize oil, sesame oil, avocado oil, coriander oil, safflower oil, safflower hybrid oil, passion-flower oil, olive oil, apricot-kernel oil, macadamia oil, musk-rose oil, fruit-pip (grape, blackcurrant, orange, kiwi fruit) oil, linseed oil, evening-primrose oil, rice-bran oil, groundnut oil, hazelnut oil, pistachio oil, palm oil, chia oil, shea oil and mixtures thereof.

According to a preferred embodiment of the invention, a vegetable oil is used having a palmitic acid content of greater than 5% by weight, preferably greater than 10% by weight (based on the total weight of the oil) and/or an oleic acid content of greater than 10% by weight, preferably greater than 15% by weight (based on the total weight of the oil), since an oil of this kind has better heat stability with respect to oxidation. As oils of this type, sunflower hybrid oil, palm oil, and apricot-kernel oil may be mentioned.

The salicylic acid derivative may be solubilized in the vegetable oil or mixture of vegetable oils in the heated state, e.g., at a temperature of approximately 60° C. to 100° C., preferably 80° C. to 85° C. The solution obtained may then be introduced into a cosmetic and/or dermatological composition, which can be a dispersion of lipid vesicles, an oil-in-water (O/W) or water-in-oil (W/O) emulsion, or an oily solution, the emulsion or solution optionally containing lipid vesicles.

The amount of salicylic acid derivative which can be dissolved depends on the vegetable oil used and the amount of this vegetable oil in the composition. The salicylic acid derivative is preferably present in an amount of from 0.01 to 10% by weight, more preferably from 0.05 to 5% by weight, based on the total weight of the composition.

Depending on the amount of salicylic acid derivative used and to avoid possible recrystallization on long-term storage, a small amount of solvent may be added to the cosmetic and/or dermatological composition. Such solvents include lower alcohols such as ethanol or isopropanol, octyldodecanol, ethylene glycol, propylene glycol, short-chain ($<C_{12}$) fatty alcohols, and short-chain ($<C_{12}$) esters, such as methyl acetate, ethyl acetate, and butyl acetate. The amount of added solvent is dependent on the amount of salicylic acid derivative introduced: the salicylic acid derivative/solvent weight ratio is suitably from 1:2.5 to 1:10, preferably 1:4 to 1:8.

When the composition is an O/W or W/O emulsion, the composition typically contains an O/W or W/O emulsifier. As O/W emulsifiers, there may be mentioned, in particular (CTFA): cetearyl glucoside sold under the name Montanov 68 by the company SEPPIC, PEG-40 stearate sold under the name Myrj 52 by the company ICI, sorbitan tristearate sold under the name Span 65 by the company ICI, sorbitan stearate sold under the name Span 60 by the company ICI, polysorbate 60 sold under the name Tween 60 by the company ICI, the sorbitan stearate/sucrose cocoate mixture sold under the name Arlatone 21-21 by the company ICI, and PPG-3 myristyl ether sold under the name Emcol 249-3K by the company Witco, which ether can also serve as a solvent.

As a W/O emulsifier, there may be mentioned, in particular, the polyglyceryl-4 isostearate/cetyldimethicone copolyol/hexyl laurate mixture sold under the name Abil WE 09 by the company Goldschmidt.

The emulsifier content can range from 0.1 to 10% by weight, preferably from 0.5% to 5% by weight, based on the total weight of the composition.

In the dispersions of lipid vesicles, the emulsifier consists of vesicles of ionic lipids (hydrogenated lecithin combined with oxyethylenated soya bean sterol) and/or nonionic lipids.

Moreover, the compositions of the present invention can contain, in the fatty phase, in addition to the salicylic acid derivative solubilized in the vegetable oil or oils, mineral oils (liquid petrolatum), synthetic oils, silicone oils (cyclomethicone), perfluorinated oils (perfluoro polyethers), fatty alcohols (stearyl alcohol, cetyl alcohol) and fatty acids (stearic acid).

When the composition takes the form of an oily solution, the non-vegetable oils are used in the proportion of 5 to 95% by weight, preferably 20 to 75% by weight, based on the total weight of the composition.

In the W/O emulsions, the fatty phase typically represents from 20 to 70% by weight, preferably 30 to 60% by weight, based on the total weight of the composition. In the O/W emulsions, the fatty phase traditionally represents from 5 to 40% by weight, preferably 15 to 30% by weight, based on the total weight of the composition.

Moreover, the compositions of the present invention can contain adjuvants which are customary in the cosmetics field, such as preservatives, perfumes, hydrophilic or lipophilic gelling agents, colorant substances and hydrophilic or lipophilic active agents. The amounts of these different adjuvants used are those conventionally used in the cosmetics and/or dermatological field, and for example from 0.01 to 10% by weight, preferably 0.05 to 5% by weight, based on the total weight of the composition. These adjuvants, depending on their nature, may be introduced into the fatty phase, into the aqueous phase and/or into the lipid vesicles.

As hydrophilic active agents, it is possible to use proteins or protein hydrolysates, amino acids, polyols, especially glycerol or sorbitol, urea, alpha-hydroxy acids, salicylic acid, sugars and sugar derivatives.

As lipophilic active agents, it is possible to use retinol (vitamin A) and its derivatives, tocopherol (vitamin E) and its derivatives, essential fatty acids, ceramides and essential oils.

Advantageously, adjuvants which decrease the irritant effect of salicylic acid derivatives are chosen. To this end, essential fatty acids such an linoleic acid and linolenic acid, ceramides such as oleoyldihydrosphingosine, glycoceramides and pseudoceramides are used in particular. Moreover, these adjuvants prevent recrystallization of the salicylic acid derivatives, and hence improve their solubilization.

As hydrophilic gelling agents, xanthan gum, carboxyvinyl polymers, cellulose derivatives, pectins and polyacrylamides, especially the polyacrylamide/C13-14 isoparaffin/laureth-7 mixture sold under the name Sepigel 305 by the company SEPPIC, may be mentioned.

UV screening agents having a lipophilic or hydrophilic property, and titanium or zinc oxide, may also be included in the present compositions.

The present invention also provides a method for the cosmetic treatment of acne and of ageing which comprises applying the present composition to the skin. The amount of the present composition which is applied to the skin will of course depend on the amount of salicylic acid derivative present in the composition. Typically, good results are achieved when sufficient composition is applied to result in $1\times10^{-6}$ to 0.01 g, preferably $5\times10^{-6}$ to 0.005 g, of the salicylic acid derivative being applied per 1 cm$^2$ of skin being treated.

Other features of the invention will become apparent in the course of the following descriptions of exemplary embodiments which are given for illustration of the invention and are not intended to be limiting thereof.

EXAMPLES

In the following examples all amounts are given in % by weight based on the total weight of the composition. The term "qs 100%" means that the ingredient is added in an amount sufficient to make the sum of the amounts for all ingredients of the composition equal 100% by weight.

EXAMPLE 1

W/O Emulsion

| Phase A: | |
|---|---|
| Polyglyceryl-4 isostearate/cetyldi- methicone copolyol/hexyl laurate (Abil WE 09) | 4.00 |
| Heptamethylnonane | 5.00 |
| Sunflower oil | 9.10 |
| Musk-rose oil | 0.59 |
| Blackcurrant-pip oil | 0.30 |
| Cyclomethicone | 3.50 |
| 5-n-Octanoylsalicylic acid | 1.00 |
| Perfume | 0.15 |
| Preservative (propylparaben) | 0.10 |
| Phase B: | |
| Magnesium sulfate | 0.65 |
| Glycerol | 10.00 |
| Water | 62.65 |
| Phase C: | |
| Cellulose gum | 0.50 |
| Preservative (quaternium-15) | 0.10 |
| Water | qs 100% |

Procedure:

The constituents of phase A are heated to 80° C. until the different constituents have dissolved completely. The mixture is cooled to 65° C. Phase B is then heated to 65° C. and poured into phase A with stirring; phase C is added and the mixture is then cooled to 25° C.

The composition obtained is a skin care cream having good nourishing and hydrating properties.

EXAMPLE 2

O/W Emulsion

| Phase A: | |
|---|---|
| Cetearyl glucoside (Montanov 68) | 0.18 |
| 5-n-Octanoylsalicylic acid | 1.5 |
| Apricot-kernel oil | 15.5 |
| Stearyl alcohol | 2.6 |
| Cetyl alcohol | 0.7 |
| Stearic acid | 1.0 |
| Octylmethoxy cinnamate (screening agent) | 1.0 |
| Preservative (butylparaben) | 0.15 |
| Octyldodecanol | 5.0 |
| Cyclomethicone | 5.0 |
| Phase B: | |
| Glycerol | 3.0 |
| Preservative (methylparaben) | 0.2 |
| Water | 50.0 |
| Phase C: | |
| Polyacrylamide/C13–14 isoparaffin/ laureth-7 (Sepigel 305) | 0.6 |
| Phase D: | |
| Water | qs 100% |

Procedure:

The constituents of phase A, and those of phase B are heated to 80° C. The phases are cooled to 70° C., and phase A is then poured into phase B with stirring. Phase C is added, followed by phase D at 60° C., with stirring. A face care cream having hydrating and protective properties is obtained.

EXAMPLE 3

O/W Emulsion

| Phase A: | |
|---|---|
| 5-n-octanoylsalicylic acid | 1.0 |
| Oleoyldihydrosphingosine | 0.10 |
| Sunflower oil | 15.0 |
| Phase B: | |
| Blackcurrant-pip oil | 1.00 |
| Sorbitan tristearate (Span 65) | 0.90 |
| PEG-40 stearate (Myrj 52) | 2.00 |
| Cetyl alcohol | 4.00 |
| Glyceryl stearate (co-emulsifier) | 3.00 |
| Preservative (propylparaban) | 0.10 |
| Phase C: | |
| Glycerol | 3.0 |
| Preservative (mothylparaben) | 0.2 |
| Water | qs 100% |

Procedure:

Phase A is heated to 80° C., and phase B is heated to 85° C., and they are then mixed. The mixture is added to phase C with stirring at 65° C. The resulting mixture is cooled to room temperature. A hydrating and nourishing body care cream is obtained.

EXAMPLE 4

O/W Emulsion

| Phase A: | |
|---|---|
| 5-n-Octanoylsalicylic acid | 0.50 |
| Heptamethylnonane | 5.00 |
| Sunflower oil | 15.00 |
| Musk-rose oil | 0.65 |
| Stearyl alcohol | 0.50 |
| Preservative (propylparaben) | 0.10 |
| Phase B: | |
| Polyacrylamide/C13–14 isoparaffin/ | 1.30 |

|  |  |
|---|---|
| laureth-7 (Sepigel 305) | |
| Phase C: | |
| Sorbitan stearate/sucrose cocoate (Arlatone 21-21) | 2.50 |
| Glycerol | 3.00 |
| Perfume | 0.20 |
| Preservative | 0.20 |
| Water | qs 100% |

Procedure:

Phase A is heated to 80° C. It is cooled to 70° C. and then poured into phase C with stirring. Phase B in added at 60° C., with stirring. The mixture in cooled with stirring. A hydrating fluid face cream is obtained.

EXAMPLE 5

Skin Care Oil

|  |  |
|---|---|
| Sunflower oil | 80.6 |
| Musk-rose oil | 5.3 |
| Blackcurrant-pip oil | 2.7 |
| Cyclomethicone | 10.0 |
| 5-n-Octanoylsalicylic acid | 1.0 |
| Perfume | 0.3 |
| oleoyldihydrosphingosine | 0.1 |

Procedure:

The mixture of vegetable oils, 5-n-octanoylsalicylic acid and oleoyldihydrosphingosine is heated to 80° C.; it is cooled to 40° C., and the other constituents are then added. The oil obtained is nourishing and protective; it may be used for the face and/or body.

EXAMPLE 6

O/W Emulsion

|  |  |
|---|---|
| Phase A: | |
| 5-n-octanoylsalicylic acid | 1.0 |
| Oleoyldihydrosphingosine | 0.1 |
| Apricot-kernel oil | 14.5 |
| Shea oil | 7.0 |
| PPG-3 myristyl ether (Emcol 249-3K) | 5.0 |
| Preservative (propylparaben) | 0.1 |
| Polysorbate 60 (Tween 60) | 2.5 |
| Sorbitan stearate (Span 60) | 2.5 |
| Phase B: | |
| Cyclomethicone | 4.0 |
| Xanthan gum | 0.2 |
| Carboxyvinyl polymer | 0.5 |
| Phase C: | |
| Triethanolamine (neutralizing agent) | 0.5 |
| Water | 2.0 |
| Phase D: | |
| Preservative (methylparaben) | 0.2 |
| Glycerol | 5.0 |
| Water | qs 100% |

Procedure:

The constituents of phase A are melted at 85° C. The phase in then cooled to 70° C., and phases B and then C and D are introduced into it with stirring. The mixture is cooled to room temperature. A hydrating day cream which acts against the natural ageing of the skin is obtained.

EXAMPLE 7

Face Care Cream in the Form of a Dispersion of Liposomes

|  |  |
|---|---|
| Phase A: | |
| Polyoxyethylenated soya bean sterol | 0.8 |
| Hydrogenated lecithin | 1.2 |
| Phase B: | |
| Water | 28.2 |
| Phase C: | |
| Apricot-kernel oil | 14.5 |
| oleoyldihydrosphingosine | 0.1 |
| 5-n-octanoylsalicylic acid | 0.5 |
| Perfume | 0.2 |
| Phase D: | |
| Glycerol/carboxyvinyl polymer/water (67.5:1:31.5) | 5.0 |
| Preservative | 0.5 |
| Polyacrylamide/C13–14 isoparaffin/laureth-7 (Sepigel 305) | 2.0 |
| Water | qs 100% |

Procedure:

The constituents of phase A are melted at 100° C.; phase B is added gradually at 80° C. with stirring, and the mixture is then subjected twice to homogenization at high pressure to form vesicles. The constituents of phase C are heated to 80°–85° C. until solubilization is complete. Phase C is cooled and added to the mixture of phases A and B. The resulting mixture is subjected twice to homogenization at high pressure and then cooled, and phase D is added with stirring.

A hydrating cream which is effective for combating the natural ageing of the skin in obtained.

EXAMPLE 8

O/W Emulsion

|  |  |
|---|---|
| Phase A: | |
| 5-n-Octanoylsalicylic acid | 1 |
| Sunflower oil | 4.2 |
| Musk-rose oil | 0.41 |
| Blackcurrant-pip oil | 0.21 |
| Cyclomethicone | 4 |
| Stearyl alcohol | 0.6 |
| Cetyl alcohol | 0.6 |
| Stearic acid | 0.6 |
| Preservative | 0.15 |
| Octyldodecanol | 5 |
| PEG-20 Stearate | 1.2 |
| PEG-100 Stearate | 0.6 |
| Glyceryl Stearate | 0.6 |
| Phase B: | |
| Glycerol | 4 |
| Carboxyvinyl polymer | 0.05 |
| Sodium hydroxide | 0.024 |
| Water | qs 100% |
| Phase C: | |
| Polyacrylamide/C13–14 isoparaffin/laureth-7 (Sepigel 305) | 0.9 |

Procedure:

The constituents of phase A are heated to 80° C., and the constituents of phase B are heated to 65° C. Phase A is cooled to 65° C. and poured into phase B with stirring. Phase C is added, with stirring. A face care cream having nourishing properties is obtained.

The present application is based on French Patent Application 94-00175 filed on Jan. 10, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A process for solubilizing a salicylic acid derivative, comprising mixing a salicylic acid derivative with at least one vegetable oil, in a weight ratio of vegetable oil to salicylic acid derivative greater than 5 to form a single phase solution of said salicylic acid derivative and said vegetable oil, wherein said salicylic acid derivative has the formula

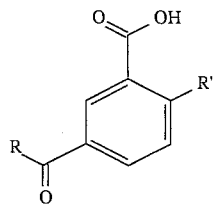

wherein R is a saturated linear, branched, or cyclic aliphatic group having from 3 to 11 carbon atoms; an unsaturated linear, branched, or cyclic hydrocarbon group having from 3 to 17 carbon atoms and having one or more conjugated or unconjugated ethylenic double bonds; a saturated linear, branched, or cyclic aliphatic group having from 3 to 11 carbon atoms and substituted with at least one substituent selected from the group consisting of halogens, trifluoromethyl, hydroxyl, hydroxyl esterified with a carboxylic acid having from 1 to 6 carbon atoms, carboxyl, and carboxyl esterified with a lower alcohol having from 1 to 6 carbon atoms; or an unsaturated linear, branched, or cyclic hydrocarbon group having from 3 to 17 carbon atoms and having one or more conjugated or unconjugated ethylenic double bonds and substituted with at least one substituent selected from the group consisting of halogens, trifluoromethyl, hydroxyl, hydroxyl esterified with a carboxylic acid having from 1 to 6 carbon atoms, carboxyl, and carboxyl esterified with a lower alcohol having from 1 to 6 carbon atoms; and R' represents a hydroxyl group or an ester function of formula (II):

where $R_1$ is a saturated or unsaturated aliphatic group having from 1 to 18 carbon atoms.

2. The process of claim 1, wherein said weight ratio of vegetable oil to salicylic acid derivative is greater than 10.

3. The process of claim 1, wherein said vegetable oil is at least one oil selected from the group consisting of sunflower oil, sunflower hybrid oil, wheat-germ oil, jojoba oil, maize oil, sesame oil, avocado oil, coriander oil, safflower oil, safflower hybrid oil, passion-flower oil, olive oil, apricot-kernel oil, macadamia oil, musk-rose oil, fruit-pip oil, linseed oil, evening-primrose oil, rice-bran oil, groundnut oil, hazelnut oil, pistachio oil, palm oil, chia oil, shea oil, and mixtures thereof.

4. The process of claim 1, wherein said vegetable oil is an oil having an oleic acid content of more than 10% by weight, based on the weight of the oil.

5. The process of claim 1, wherein said vegetable oil is an oil having a palmitic acid content of more than 5% by weight, based on the weight of the oil.

6. The process of claim 1, wherein said mixing is carried out with heating.

7. The process of claim 6, wherein said mixing is carried out at a temperature of 60° to 100° C.

8. A cosmetic and/or dermatological composition comprising at least one salicylic acid derivative of the formula (I)

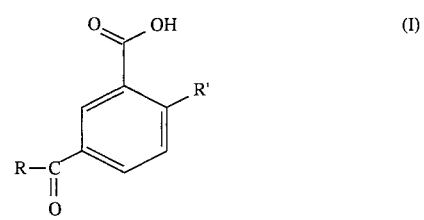

wherein R is a saturated linear, branched, or cyclic aliphatic group having from 3 to 11 carbon atoms; an unsaturated linear, branched, or cyclic hydrocarbon group having from 3 to 17 carbon atoms and having one or more conjugated or unconjugated ethylenic double bonds; a saturated linear, branched, or cyclic aliphatic group having from 3 to 11 carbon atoms and substituted with at least one substituent selected from the group consisting of halogens, trifluoromethyl, hydroxyl, hydroxyl esterified with a carboxylic acid having from 1 to 6 carbon atoms, carboxyl, and carboxyl esterified with a lower alcohol having from 1 to 6 carbon atoms; or an unsaturated linear, branched, or cyclic hydrocarbon group having from 3 to 17 carbon atoms and having one or more conjugated or unconjugated ethylenic double bonds and substituted with at least one substituent selected from the group consisting of halogens, trifluoromethyl, hydroxyl, hydroxyl esterified with a carboxylic acid having from 1 to 6 carbon atoms, carboxyl, and carboxyl esterified with a lower alcohol having from 1 to 6 carbon atoms; and R' represents a hydroxyl group or an ester function of formula (II):

where $R_1$ is a saturated or unsaturated aliphatic group having from 1 to 18 carbon atoms; and at least one vegetable oil as a single phase solution of salicylic acid derivative and vegetable oil, in a weight ratio of vegetable oil to salicylic acid derivative of greater than 5.

9. A method for the cosmetic treatment of acne or ageing, comprising applying to the skin a cosmetic composition comprising at least one salicylic acid derivative of the formula (I)

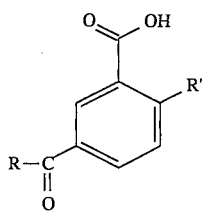

(I)

wherein R is a saturated linear, branched, or cyclic aliphatic group having from 3 to 11 carbon atoms; an unsaturated linear, branched, or cyclic hydrocarbon group having from 3 to 17 carbon atoms and having one or more conjugated or unconjugated ethylenic double bonds; a saturated linear, branched, or cyclic aliphatic group having from 3 to 11 carbon atoms and substituted with at least one substituent selected from the group consisting of halogens, trifluoromethyl, hydroxyl, hydroxyl esterified with a carboxylic acid having from 1 to 6 carbon atoms, carboxyl, and carboxyl esterified with a lower alcohol having from 1 to 6 carbon atoms; or an unsaturated linear, branched, or cyclic hydrocarbon group having from 3 to 17 carbon atoms and having one or more conjugated or unconjugated ethylenic double bonds and substituted with at least one substituent selected from the group consisting of halogens, trifluoromethyl, hydroxyl, hydroxyl esterified with a carboxylic acid having from 1 to 6 carbon atoms, carboxyl, and carboxyl esterified with a lower alcohol having from 1 to 6 carbon atoms; and R' represents a hydroxyl group or an ester function of formula (II):

(II)

where $R_1$ is a saturated or unsaturated aliphatic group having from 1 to 18 carbon atoms; and at least one vegetable oil as a single phase solution of salicylic acid derivative and vegetable oil, in a weight ratio of vegetable oil to salicylic acid derivative of greater than 5.

10. The cosmetic composition of claim 8, wherein said weight ratio of vegetable oil to salicylic acid derivative is greater than 10.

11. The cosmetic composition of claim 8, wherein said vegetable oil is at least one oil selected from the group consisting of sunflower oil, sunflower hybrid oil, wheat-germ oil, jojoba oil, maize oil, sesame oil, avocado oil, coriander oil, safflower oil, safflower hybrid oil, passion-flower oil, olive oil, apricot-kernel oil, macadamia oil, musk-rose oil, fruit-pip oil, linseed oil, evening-primrose oil, rice-bran oil, groundnut oil, hazelnut oil, pistachio oil, palm oil, chia oil, shea oil, and mixtures thereof.

12. The cosmetic composition of claim 8, wherein said vegetable oil is an oil having an oleic acid content of more than 10% by weight, based on the weight of the oil.

13. The cosmetic composition of claim 8, wherein said vegetable oil is an oil having a palmitic acid content of more than 5% by weight, based on the weight of the oil.

14. The cosmetic composition of claim 8, which is in the form of an O/W emulsion.

15. The cosmetic composition of claim 8, which is in the form of an oily solution.

16. The cosmetic composition of claim 8, which is in the form of a dispersion of lipid vesicles.

17. The cosmetic composition of claim 8, wherein said salicylic acid derivative is 5-n-octanoylsalicylic acid.

18. The cosmetic composition of claim 8, further comprising an adjuvant selected from the group consisting of ceramides, pseudoceramides, glycoceramides and essential fatty acids.

* * * * *

UNITED STATES PATENT AND TRADEMARK OFFICE
CERTIFICATE OF CORRECTION

PATENT NO. : 5,558,871
DATED : September 24, 1996
INVENTOR(S) : Jacqueline Griat, et al.

Page 1 of 4

It is certified that error appears in the above-indentified patent and that said Letters Patent is hereby corrected as shown below:

Column 11, lines 1-9,

"

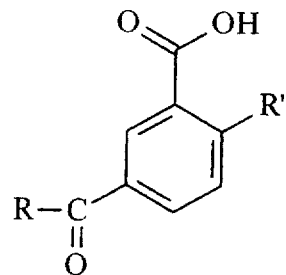

"

should read

--

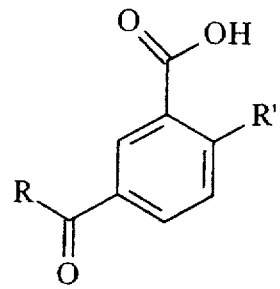

--.

UNITED STATES PATENT AND TRADEMARK OFFICE
CERTIFICATE OF CORRECTION

PATENT NO. : 5,558,871
DATED : September 24, 1996
INVENTOR(S) : Jacqueline Griat, et al.

It is certified that error appears in the above-indentified patent and that said Letters Patent is hereby corrected as shown below:

Column 6, line 42, "(mothylparaben) should read -- (methylparaben)".

Column 7, line 64, "phase in then" should read -- phase is then --.

Column 10, lines 15-24,

"
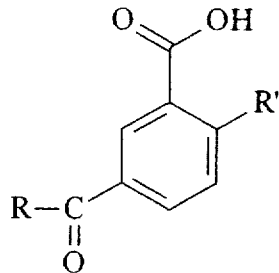
"

should read
--
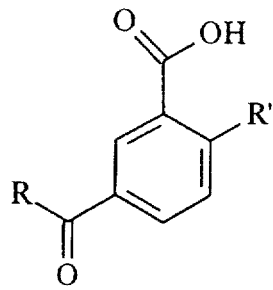
--.

UNITED STATES PATENT AND TRADEMARK OFFICE
CERTIFICATE OF CORRECTION

PATENT NO. : 5,558,871
DATED : September 24, 1996
INVENTOR(S) : Jacqueline Griat, et al.

It is certified that error appears in the above-indentified patent and that said Letters Patent is hereby corrected as shown below:

Column 2, lines 36-44,

"
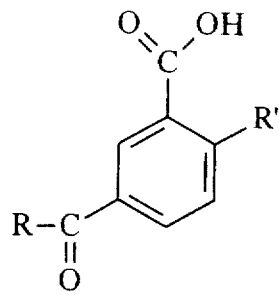
"

Should read --

UNITED STATES PATENT AND TRADEMARK OFFICE
CERTIFICATE OF CORRECTION

PATENT NO. : 5,558,871
DATED : September 24, 1996
INVENTOR(S) : Jacqueline Griat, et al.

It is certified that error appears in the above-indentified patent and that said Letters Patent is hereby corrected as shown below:

--

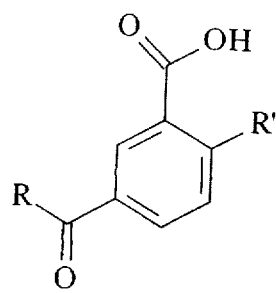

--.

Signed and Sealed this

Fourth Day of August, 1998

Attest:

BRUCE LEHMAN

Attesting Officer

Commissioner of Patents and Trademarks